United States Patent
Jimenez et al.

(10) Patent No.: US 9,801,710 B2
(45) Date of Patent: Oct. 31, 2017

(54) COLLAPSIBLE CARDIAC IMPLANT AND DEPLOYMENT SYSTEM AND METHODS

(71) Applicant: Edwards Lifesciences Corporation, Irvine, CA (US)

(72) Inventors: Teodoro S. Jimenez, Irvine, CA (US); Mark Dehdashtian, Irvine, CA (US); Raffaele Mazzei, Carlsbad, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 428 days.

(21) Appl. No.: 14/327,441

(22) Filed: Jul. 9, 2014

(65) Prior Publication Data

US 2015/0073537 A1    Mar. 12, 2015

Related U.S. Application Data

(60) Provisional application No. 61/844,409, filed on Jul. 9, 2013.

(51) Int. Cl.
    *A61F 2/24* (2006.01)
(52) U.S. Cl.
    CPC .......... *A61F 2/2409* (2013.01); *A61F 2/2448* (2013.01); *A61F 2/2466* (2013.01); *A61F 2220/0091* (2013.01); *A61F 2230/0091* (2013.01); *A61F 2230/0095* (2013.01)
(58) Field of Classification Search
    CPC .... A61F 2/2466; A61F 2/2448; A61F 2/2409; A61F 2/24; A61F 2220/0091; A61F 2230/0095; A61F 2230/0091
    See application file for complete search history.

(56) References Cited

U.S. PATENT DOCUMENTS

| | | | |
|---|---|---|---|
| 4,917,698 A | 4/1990 | Carpentier et al. | |
| 5,041,130 A | 8/1991 | Cosgrove et al. | |
| 5,061,277 A | 10/1991 | Carpentier et al. | |
| 5,064,431 A | 11/1991 | Gilbertson et al. | |
| 5,104,407 A | 4/1992 | Lam et al. | |
| 5,201,880 A | 4/1993 | Wright et al. | |
| 5,290,300 A | 3/1994 | Cosgrove et al. | |
| 5,350,420 A | 9/1994 | Cosgrove et al. | |
| 5,972,030 A * | 10/1999 | Garrison | A61B 17/00234 623/2.11 |
| 6,174,332 B1 * | 1/2001 | Loch | A61F 2/2445 623/2.37 |
| 6,183,512 B1 * | 2/2001 | Howanec, Jr. | A61F 2/2451 623/2.36 |
| 6,283,127 B1 * | 9/2001 | Sterman | A61B 17/00234 128/898 |

(Continued)

*Primary Examiner* — Eric Rosen
*Assistant Examiner* — Son Dang
(74) *Attorney, Agent, or Firm* — Guy Cumberbatch

(57) ABSTRACT

A collapsible device, such as an annuloplasty ring or prosthetic heart valve, is configured to be collapsed prior to being introduced into a patient via minimally-invasive access points such as port holes or intercostal incisions. A holder is configured to hold the collapsible device, and to selectively collapse the device for introduction into the patient and then re-enlarge the device at the desired deployment site. Collapsible devices include devices that can hingedly fold about hinge lines, and devices that can elongate to form substantially spiral forms with reduced diameters.

23 Claims, 10 Drawing Sheets

(56) References Cited

U.S. PATENT DOCUMENTS

| | | | | |
|---|---|---|---|---|
| 6,406,493 B1* | 6/2002 | Tu | ......................... | A61F 2/2448 623/2.37 |
| 6,416,548 B2* | 7/2002 | Chinn | .................... | A61F 2/2445 623/1.42 |
| 6,419,696 B1* | 7/2002 | Ortiz | ..................... | A61F 2/2409 623/2.37 |
| 7,077,861 B2* | 7/2006 | Spence | ................. | A61F 2/2445 606/99 |
| 7,101,395 B2* | 9/2006 | Tremulis | ............ | A61B 17/0401 623/2.11 |
| 7,942,927 B2* | 5/2011 | Kaye | ..................... | A61F 2/2445 623/2.11 |
| 8,099,177 B2* | 1/2012 | Dahlberg | .................. | A61N 1/05 607/127 |
| 9,237,886 B2* | 1/2016 | Seguin | .............. | A61B 17/00234 |
| 2003/0050693 A1* | 3/2003 | Quijano | ................ | A61F 2/2445 623/2.11 |
| 2006/0100697 A1* | 5/2006 | Casanova | ............. | A61F 2/2448 623/2.11 |
| 2007/0027533 A1* | 2/2007 | Douk | .................... | A61F 2/2445 623/2.11 |
| 2007/0244556 A1* | 10/2007 | Rafiee | ................... | A61F 2/2451 623/2.11 |
| 2008/0140191 A1* | 6/2008 | Mathis | .................. | A61F 2/2451 623/2.37 |
| 2009/0299471 A1* | 12/2009 | Keranen | ............... | A61F 2/2445 623/2.37 |
| 2010/0145440 A1* | 6/2010 | Keranen | ............... | A61F 2/2445 623/2.37 |
| 2011/0166649 A1* | 7/2011 | Gross | ................... | A61F 2/2445 623/2.36 |

* cited by examiner

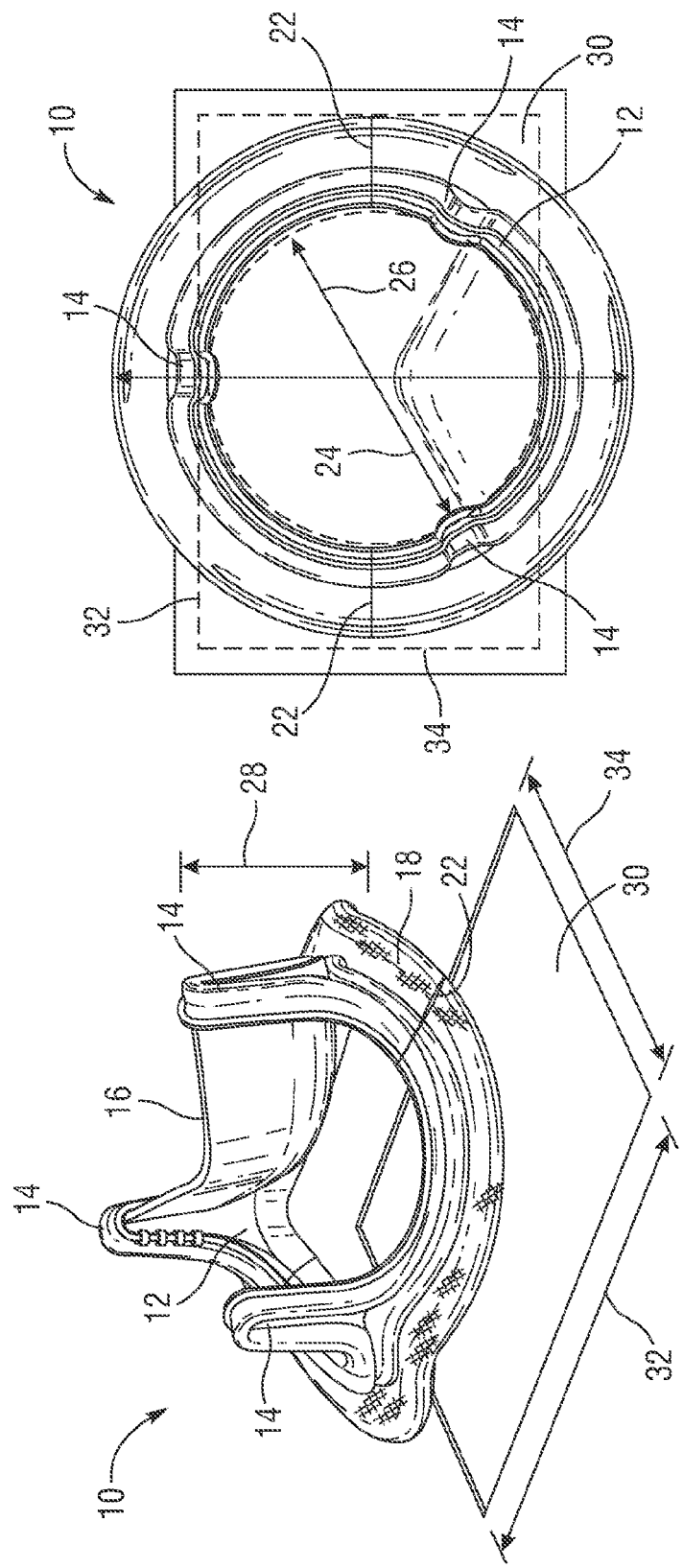

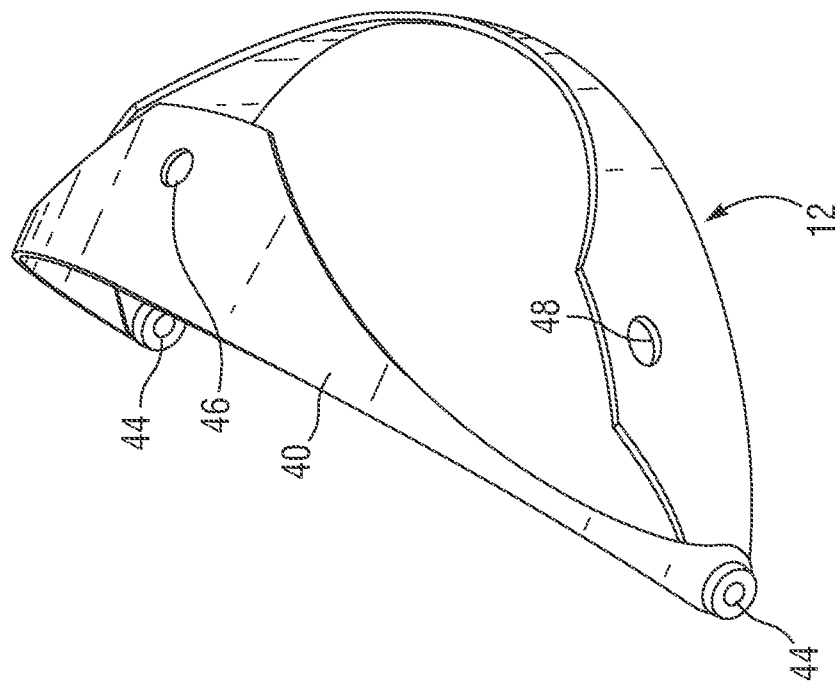
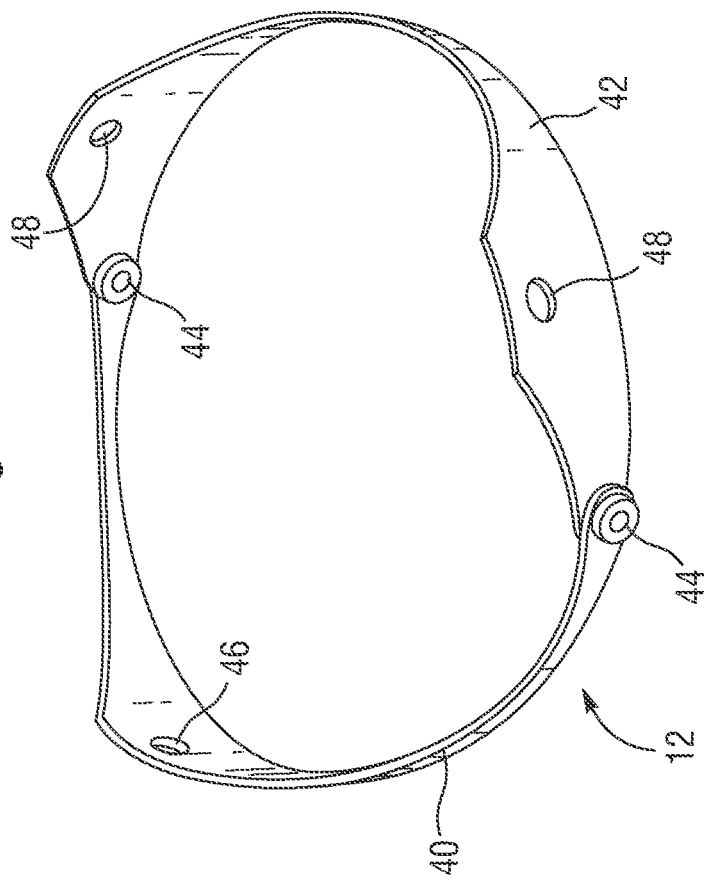

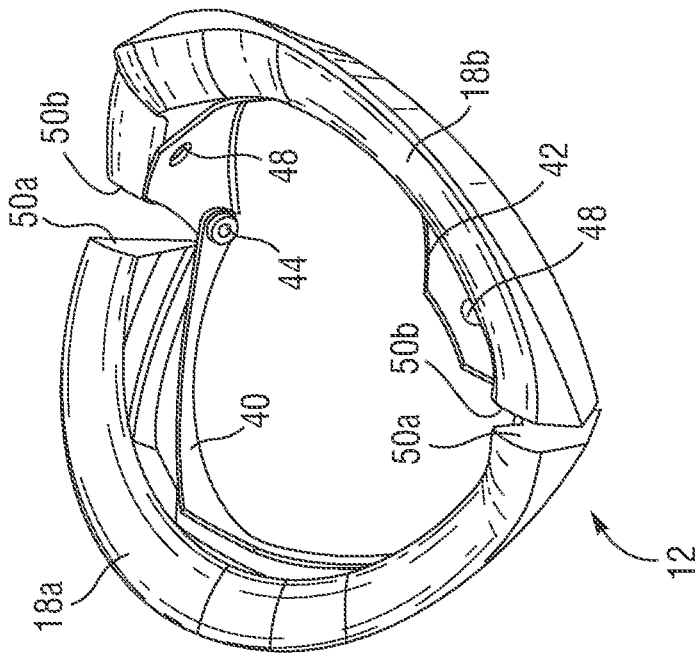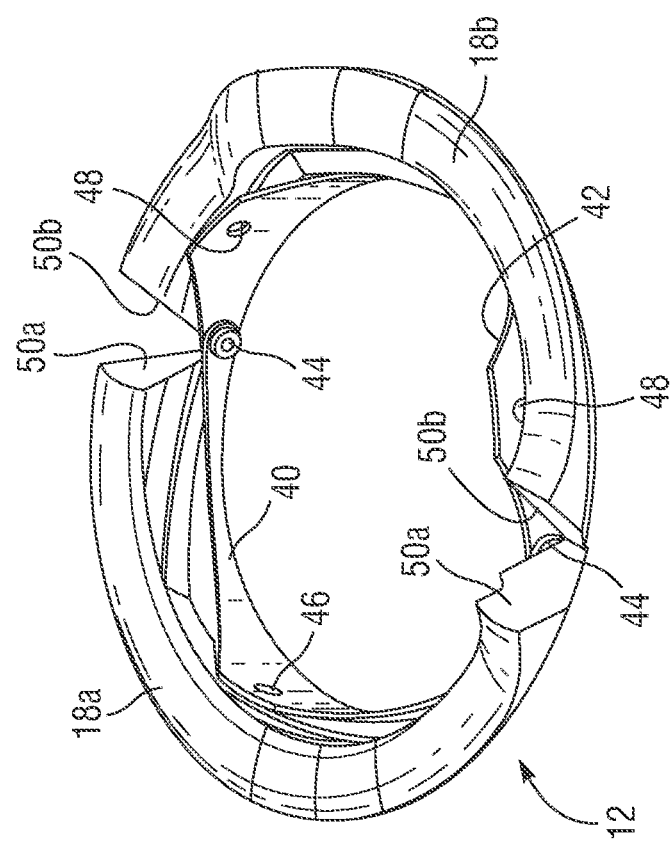

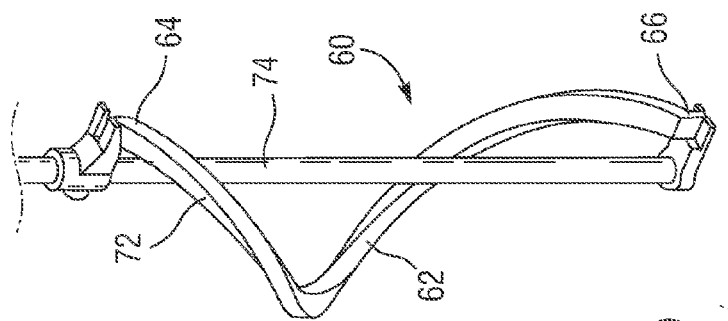
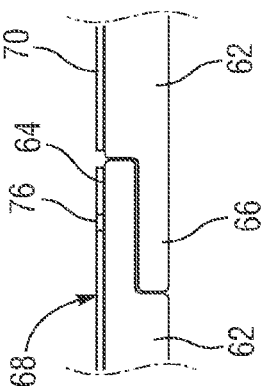
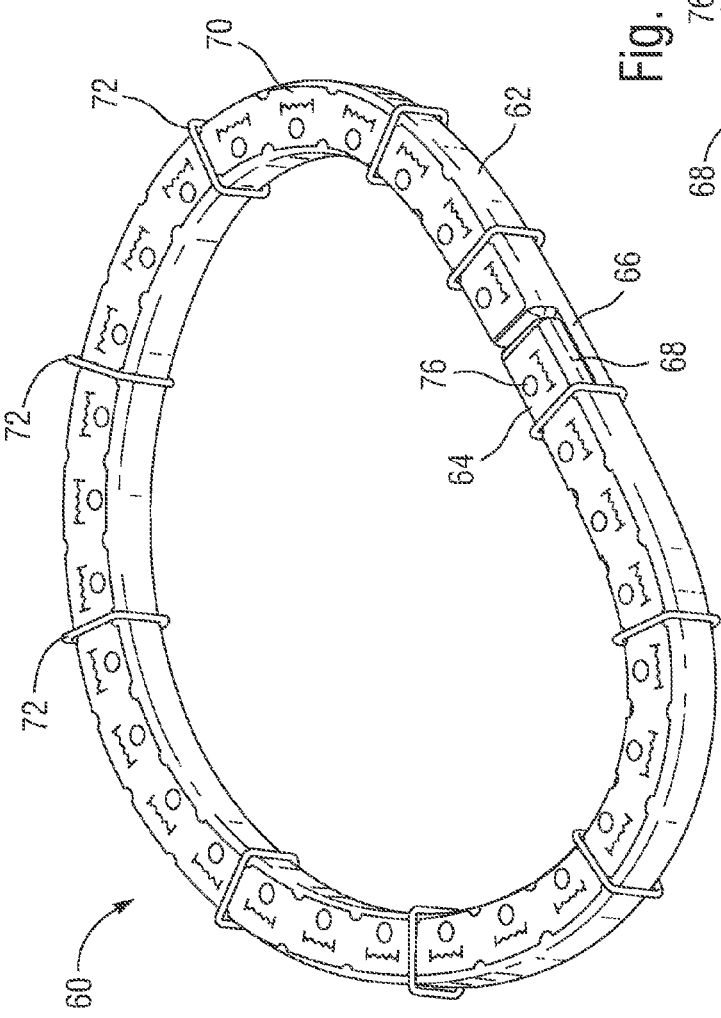

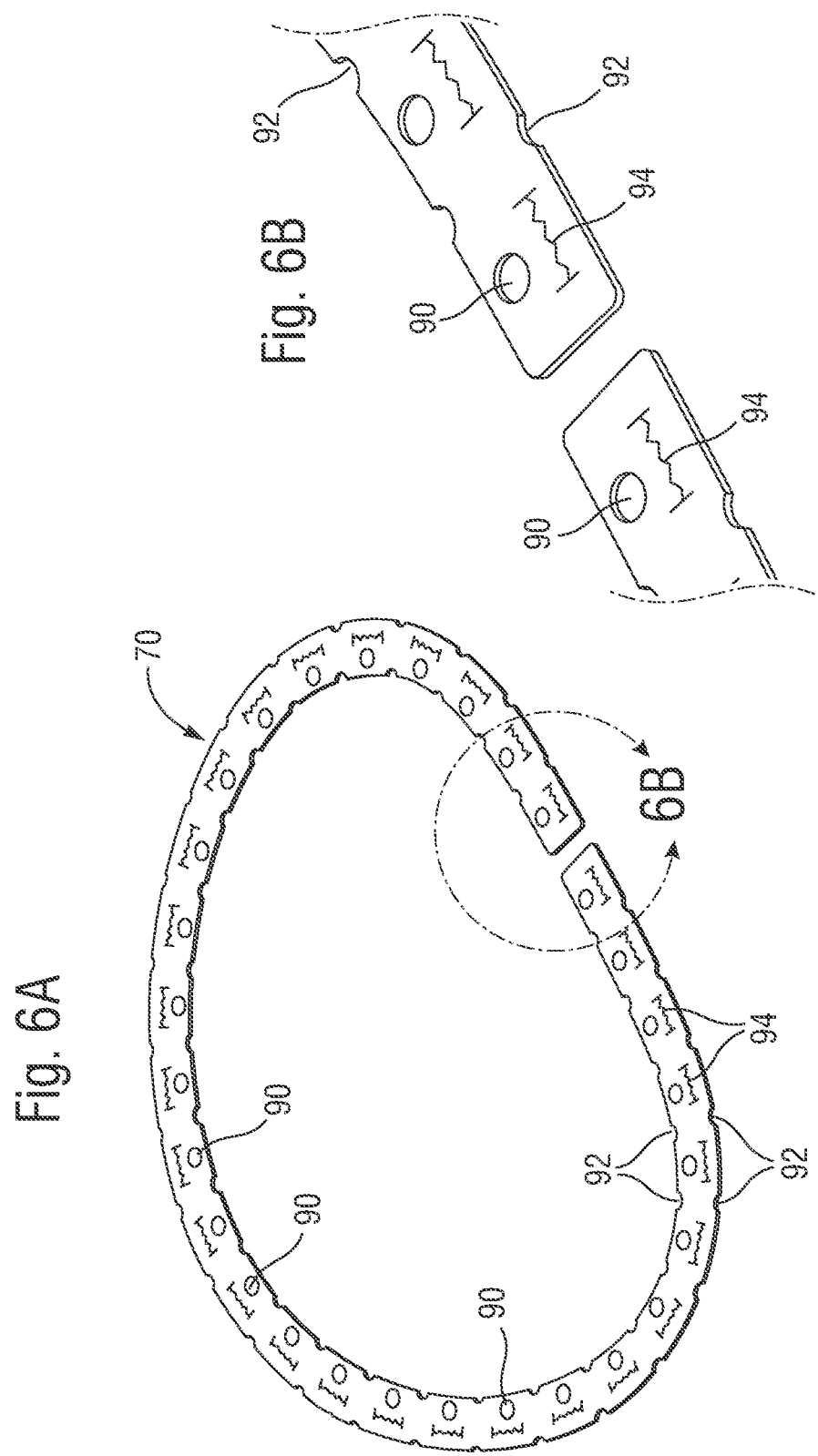

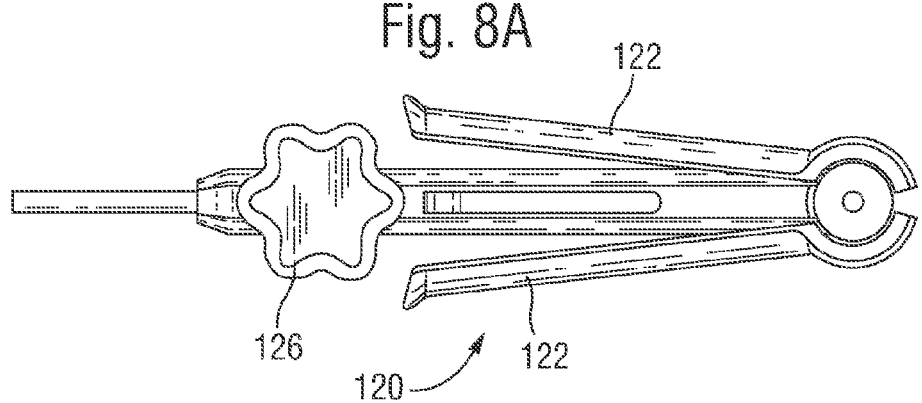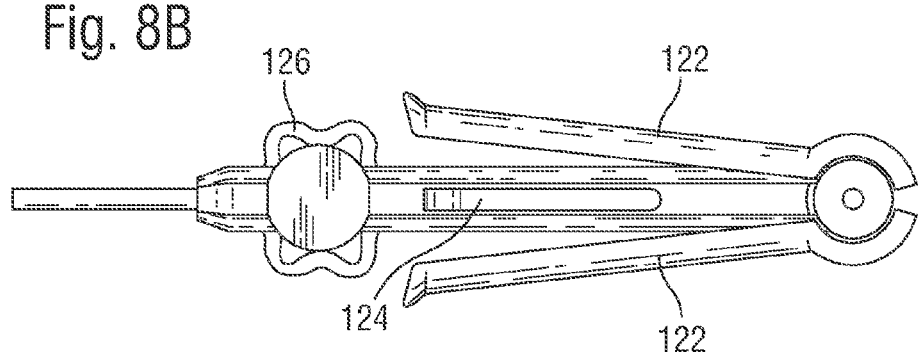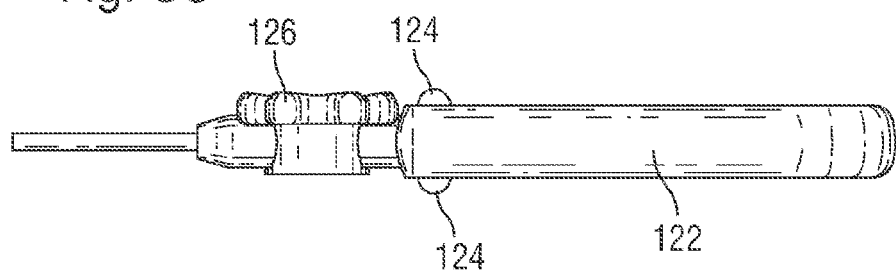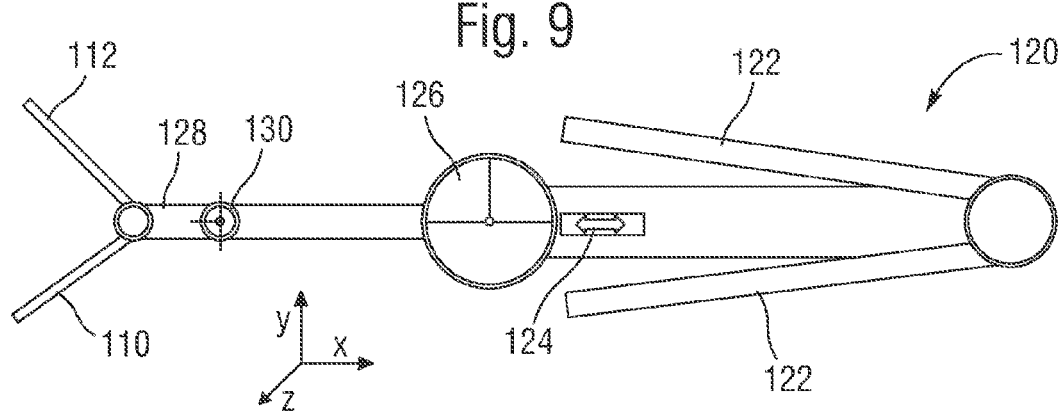

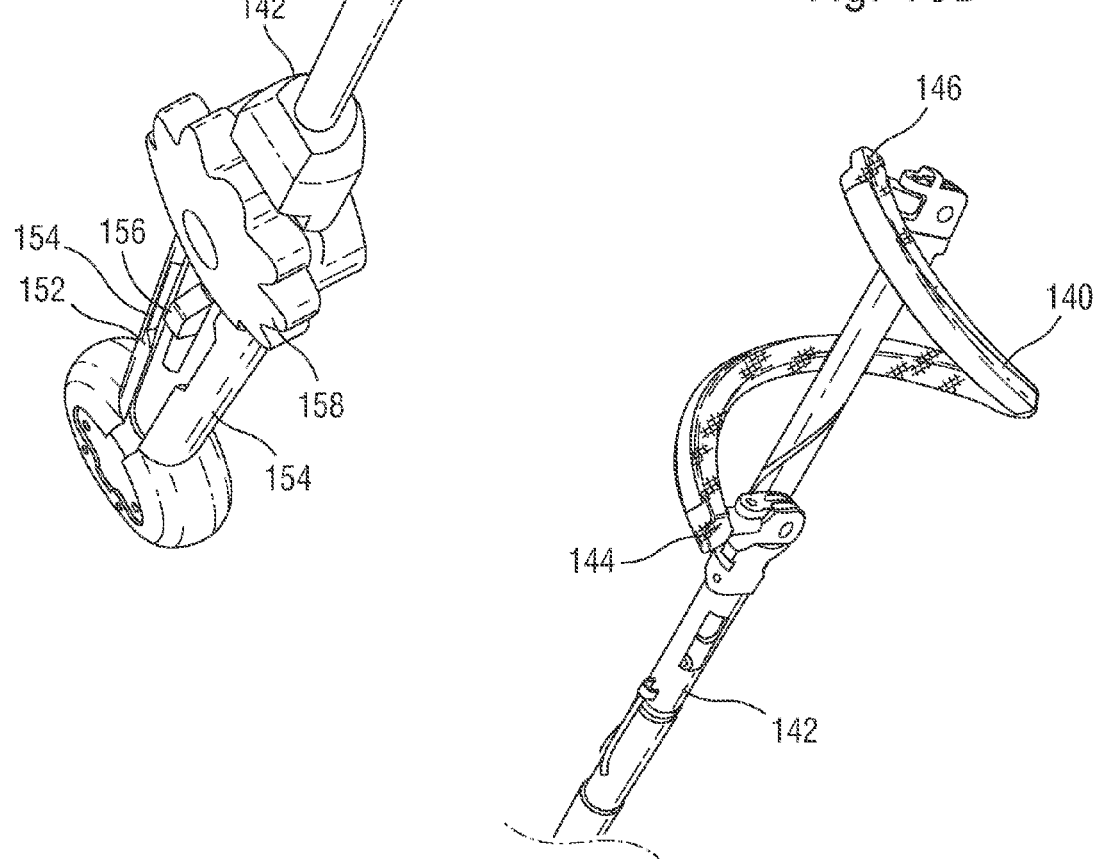

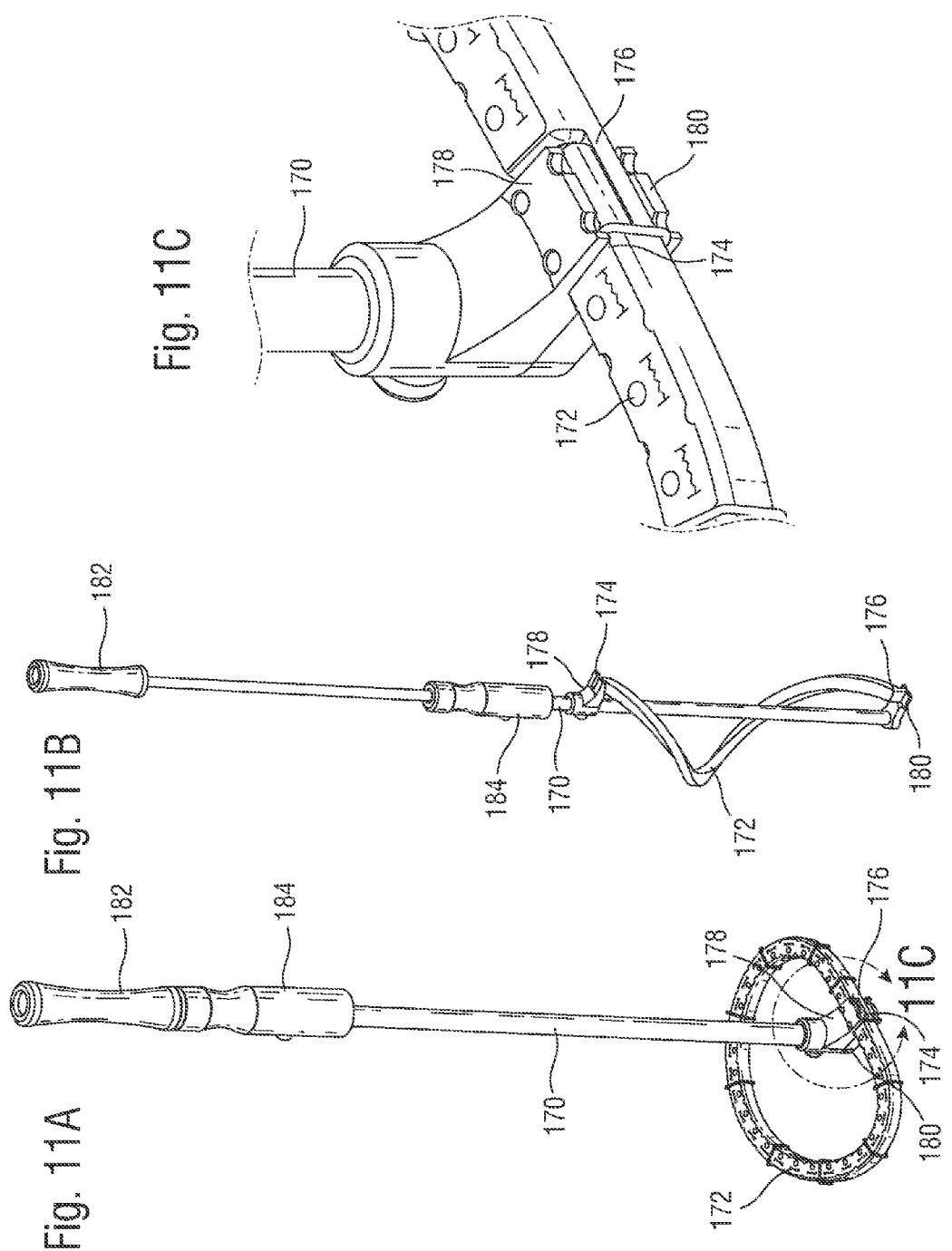

COLLAPSIBLE CARDIAC IMPLANT AND DEPLOYMENT SYSTEM AND METHODS

RELATED APPLICATIONS

The present application claims priority under 35 USC 119(e) to U.S. Provisional Application Ser. No. 61/844,409, filed Jul. 9, 2013 and entitled "Collapsible Cardiac Implant and Deployment System and Methods," the entire contents of which are hereby incorporated herein by reference.

FIELD OF THE INVENTION

The present invention relates generally to methods and devices for minimally invasive and less invasive surgical access. More particularly, the present invention provides collapsible valve implants, such as rings or prosthetic valves, including systems and methods for collapsing, delivering, and implanting such implants via small incision sites.

BACKGROUND OF THE INVENTION

Heart valve disease is a widespread condition in which one or more of the valves of the heart fails to function properly. Diseased heart valves may be categorized as either stenotic, wherein the valve does not open sufficiently to allow adequate forward flow of blood through the valve, or incompetent, wherein the valve does not close completely, causing excessive backward flow of blood through the valve when the valve is closed. A heart valve may also be both stenotic and incompetent. Valve disease can be severely debilitating and even fatal if left untreated, particularly if the diseased valve is the mitral valve (between the left atrium and left ventricle) or the aortic valve (between the left ventricle and the aorta). According to recent estimates, more than 80,000 patients are diagnosed with aortic or mitral valve disease in U.S. hospitals each year. Recent statistics show that valvular heart disease is responsible for nearly 20,000 deaths each year in the United States, and is a contributing factor in approximately 42,000 deaths. Currently, the primary treatments of valve disease are valve repair and valve replacement. Worldwide, there are approximately 300,000 heart valve replacement surgeries performed annually.

A number of interventional approaches have been developed for treating heart valve disease. For instance, annuloplasty rings have been developed in various shapes and configurations over the years to correct mitral regurgitation and other conditions which reduce the functioning of the valve. Heart valve replacement may be indicated when there is a narrowing of a native heart valve, commonly referred to as stenosis, or when the native valve leaks or regurgitates, such as when the leaflets are calcified. When replacing the valve, the native valve may be excised and replaced with either a biologic or a mechanical valve.

Annuloplasty rings are useful in treating some diseased valves where valve function can be restored by reshaping the valve annulus. In an annuloplasty procedure, the effective size of the valve annulus is contracted, and/or the valve annulus is otherwise reshaped, by attaching a prosthetic annuloplasty ring to an interior wall of the heart around the valve annulus. The annuloplasty ring may comprise an inner substrate of a metal such as stainless or titanium, and/or a flexible material such as silicone rubber or Dacron cordage, covered with a biocompatible fabric or cloth to allow the ring to be sutured to the heart tissue. The annuloplasty ring may be stiff or flexible, may be split or continuous, and may have a variety of shapes, including circular, D-shaped, C-shaped, or kidney-shaped. Examples are seen in U.S. Pat. Nos. 4,917,698, 5,061,277, 5,290,300, 5,350,420, 5,104,407, 5,064,431, 5,201,880, and 5,041,130, which are incorporated herein by reference.

Using current techniques, most valve repair and replacement procedures require a gross thoracotomy, usually in the form of a median sternotomy, to gain access into the patient's thoracic cavity. A saw or other cutting instrument is used to cut the sternum longitudinally, allowing two opposing halves of the anterior or ventral portion of the rib cage to be spread apart. A large opening into the thoracic cavity is thus created, through which the surgical team may directly visualize and operate upon the heart and other thoracic contents. Alternatively, a thoracotomy may be performed on a lateral side of the chest, wherein a large incision is made generally parallel to the ribs, and the ribs are spread apart and/or removed in the region of the incision to create a large enough opening to facilitate the surgery.

Using such open-chest techniques, the large opening provided by a median sternotomy or thoracotomy can enable the surgeon to see the diseased valve directly, and to position his or her hands within the thoracic cavity in close proximity to the exterior of the heart for cannulation of the aorta and/or coronary arteries to induce cardioplegia, manipulation of surgical instruments, removal of excised tissue, and introduction of an annuloplasty ring or a replacement valve for attachment within the heart. Most interventional techniques are conducted under general anesthesia and require that the patient's sternum be opened and the chest be spread apart to provide access to the heart. The first 2-3 days following surgery are often spent in an intensive care unit where heart functions can be closely monitored. The average hospital stay is between 1 to 2 weeks, with several more weeks to months required for complete recovery. While often very effective, the use of open-heart surgery to perform cardiac procedures may be highly traumatic to the patient.

While heart valve surgery produces beneficial results for many patients, numerous others who might benefit from such surgery are unable or unwilling to undergo the trauma and risks associated with open-chest procedures. Recently, minimally invasive surgical techniques and procedures to perform traditionally open-chest cardiac surgical procedures are gaining acceptance. A wide variety of laparoscopic, arthroscopic, endovascular, and other surgical therapies have been developed. These procedures generally utilize trocars, cannulas, catheters, or other tubular sheaths to provide an artificial lumen through which specialized tools are inserted and manipulated by the surgeon. Such minimally-invasive procedures substitute one or more relatively small port holes or other intercostals incisions through the patient's chest wall for the larger sternotomy and thoracotomy approach of conventional open-chest surgeries. A major advantage of such minimally-invasive approaches is that the procedure avoids cutting through bones or other hard tissues of the patient, instead cutting incisions only into soft tissue. Such soft tissues typically heal much faster than bones, and with less discomfort to the patient.

Annuloplasty rings and even many prosthetic valves are usually relatively small, but even their relatively small sizes can still be a challenge for introduction into and manipulation/positioning within a patient's chest cavity, particularly where it is desirable to introduce the devices into a patient via intercostal incisions in order to avoid cutting through bone. Typical intercostal incisions have widths of about 20 mm and lengths of about 30 mm. While the large length of many intercostals space may permit the length of an intercostal incision to be extended beyond 30 mm, the width of intercostal spaces prevent the creation of intercostal opening with widths beyond about 20 mm. Greater intercostal opening widths may require cutting into adjacent ribs and/or displacing adjacent ribs to the point where the bones are cracked and/or bruised by the displacement, which can increase the risk of trauma to the patient as well as extend recovery time. Accordingly, devices and handles that can be introduced through an opening of about 20 mm width may be desirable for minimally invasive procedures via intercostals incisions.

Annuloplasty ring prostheses are generally mounted on a holder assembly to facilitate their manipulation during the course of a surgical intervention and their implantation. Current holder assemblies are characterized by a number of drawbacks. A great majority of holders are configured with a rigid handle and a fixed orientation of the holder body or prosthesis carrier relative to the handle. Such a mechanical limitation does not allow the surgeon to orient the holder body relative to the handle in order to optimize the delivery of the prosthesis to the implant site. Some holder assemblies have been configured with malleable handles in an attempt to alleviate this drawback. However, such malleable handles are generally difficult to reshape in different bent configurations once they have been initially bent.

In view of actual and perceived drawbacks associated with current annuloplasty and prosthetic valve deployment techniques, there is a need for a less invasive approach and improved handle. The current invention satisfies these needs.

SUMMARY OF THE INVENTION

Preferred embodiments of the present application provide a valve ring or prosthetic valve that can be folded, crimped, or stretched for delivery into and manipulation within a patient's chest cavity, and then restored to an extended configuration for deployment at the native valve annulus. Such valves and valve rings are particularly useful for delivery via small incisions such as mini thoracotomy, right thoracotomy, or right anterior thoracotomy. Delivery systems and methods of the invention provide handles for introducing, manipulating, and deploying the collapsible valves and valve ring. Such handles may have a series of steering mechanisms that will allow for proper navigation to the deployment site.

In one aspect, the present application discloses a holder for delivering an annuloplasty ring or prosthetic valve, comprising holder configured to hold, collapse, and steer the device into the patient. The holder may have a handle with controls to provide for movement of the holder distal portion in any direction and the ability to steer the device into a desired position within the patient. The holder may preferably be configured to be operated with just one hand. The holder may itself actuate the collapse/folding/crimping/elongation of the valve ring or valve, as well as actuating restoration of the valve ring or valve to its deployed configuration. For example, the holder may fold, twist, and otherwise manipulate the device and then re-form the device back to its original shape.

A method of implanting devices in a human body, comprises creating an opening in the chest cavity of a patient; grasping a device holder having a collapsible/longitudinally elongatable device on the distal end thereof, wherein the device is a valve ring or prosthetic valve; collapsing the device by operating one or more controls of the device holder to collapse the device; after collapsing the device, advancing the collapsed device through the intercostal opening and into the patient; positioning the device at a desired deployment site in the patient; uncollapsing the device so that the device returns to a deployed configuration; securing the device to the desired deployment site in the patient; releasing the device from the device holder; and removing the device holder from the patient. The method may further include folding the device and/or elongating the device while reducing an outer diameter of the device. The device may be selected from the group comprising annuloplasty rings and prosthetic heart valves, and securing the device to the desired deployment site comprises securing the device within a native valve annulus. Securing the device to the desired deployment site may comprise suturing the device within the native valve annulus.

A collapsible intracardiac implant device of an embodiment of the invention has a support ring, the support ring comprising two half segment portions, and hinges securing the two half segment portions to each other to form a completed ring, wherein the hinges permit relative hinging movement between the two half segment portions. The device may be an annuloplasty ring and further have a first central stent structure defining a first of the half portions, a second central stent structure defining a second of the half portions, and a sewing ring extending around the support ring. A cloth cover may surround the sewing ring and first and second stent structures. A suture locking ring may be positioned on top of the support ring on the outer surface of the cloth cover, the suture locking ring having a plurality of suture holes passing from a top surface of the suture locking ring through to a bottom surface thereof, the suture holes configured to receive suture therethrough. A plurality of suture locks may be provided on the suture locking ring, wherein each suture lock is configured to receive a suture therethrough and to lock the suture in place. A suture lock may positioned on the top surface of the suture locking ring at a position immediately radially outward of each of the plurality of suture holes. A hinge lock may be provided to prevent the half segment portions from rotating with respect to each other about the hinges when the device is in an open configuration. The device may be a prosthetic heart valve and have a first central stent structure defining a first of the half portions; a second central stent structure defining a second of the half portions; a first commissural support extending upward from the first of the half portions at a midpoint between opposing ends thereof; second and third commissural supports extending upwardly from the second of the half portions at points spaced away from a midpoint of opposing ends thereof such that when the first and second half portions are rotated toward each other in an upward direction around the hinges, the first commissural support is rotated to a position in between the second and third commissural supports; and a plurality of valve leaflets, wherein each valve leaflet extends between two of the commissural supports, and wherein when the valve leaflets are configured, when the device is in an open/deployed configuration, to coapt to control fluid flow through a central orifice defined within the support ring. A hinge lock may be provided and configured to prevent the half segment portions from rotating with respect to each other about the hinges when the device is in an open configuration.

Another embodiment of a collapsible intracardiac implant device has a support ring comprising opposing ends which are positioned adjacent each other when the device is in an open/deployed configuration, wherein the opposing ends can be longitudinally displaced with respect to each other to thereby cause the support ring to transform to an elongated spiral configuration; wherein the support ring comprises a support structure which biases the support ring to the open/deployed configuration. The device may be an annuloplasty ring and have a sewing ring secured around the support structure; and a cover encapsulating the sewing ring. The device may be a prosthetic heart valve having a plurality of commissural supports extending upward from the device, wherein the commissural supports are spaced around the perimeter of the device, where one of the commissural supports comprises a first half positioned adjacent the first opposing end of the support ring and a second half positioned adjacent the second opposing end of the support ring, wherein when the opposing ends are positioned adjacent each other the first half and second half are positioned against each other and function as a single commissural support, and when the opposing ends are longitudinally displaced from each other the first half and second half are longitudinally displaced from each other. A plurality of leaflets may be provide that extends from one commissural support to another commissural support, and wherein when the device is in the open/deployed configuration the leaflets coapt to control fluid flow through a central orifice defined within the support ring, and when the device is in the elongated/spiral configuration the leaflets do not coapt. A sewing ring may be positioned on an outer perimeter of the device outside the central orifice, the sewing ring configured to receive needle and suture therethrough. A suture locking ring may be positioned on top of the sewing ring, and have a plurality of suture holes passing from a top surface of the suture locking ring through to a bottom surface thereof, the suture holes configured to receive suture therethrough; and a plurality of suture locks on the top surface of the suture locking ring, wherein each suture lock is configured to receive a suture therethrough and to lock the suture in place.

A system for delivering a device to a position in a patient according to an embodiment of the invention has a collapsible device configured to be collapsed and opened (e.g., via hinging or spiral elongation and to be implanted in a patient, and an elongated delivery holder configured to hold the device and advance the device in into the patient, the holder comprising a proximal portion having a handle with device collapsing and opening controls thereon and a distal portion configured to hold the device and to collapse and open the device responsive to operation of the opening controls of the handle. The collapsible device may be positioned on the distal portion of the holder.

Devices of the invention may be configured to collapse to have a minimal profile sufficient to be advanced through an opening of 20 mm in width.

The collapsing/tilting/tipping/steering mechanisms of the holder may include a gear train or a pulley system. In a preferred embodiment, the mechanisms may include a push/pull rod linearly movable within the handle. The holder may include a device detachment mechanism that may be configured to release clips and/or sever sutures holding the device to the holder.

Methods of implanting devices of the invention include: creating an intercostal access opening in a patient; grasping a device holder having a collapsible/longitudinally elongatable device on the distal end thereof, wherein the device is a valve ring or prosthetic valve; operating the device holder to collapse the device (e.g., in hinge or spiral elongation fashion); advance the collapsed device through the intercostal opening and into the patient; position the device at a desired deployment site in the patient; uncollapsing the device; securing the device to the desired deployment site in the patient; release the device from the device holder; and remove the device holder from the patient.

The invention can be used in various procedures. In an example of such a procedure, an intercostal opening of about 20 mm width and 30 mm or more length is created for access using surgical instruments. One or more port hole punctures are provided through which visualization (e.g., cameras) and/or ablation and/or suture catheters may be advanced for use in the procedure. The devices of the invention, as well as other instruments (such as suturing devices) may be advanced through the intercostal opening to perform a desired repair and/or implantation, which may occur on or in the patient's heart.

Further understanding of the nature and advantages of the present invention are set forth in the following description and claims, particularly when considered in conjunction with the accompanying drawings in which like parts bear like reference numerals.

BRIEF DESCRIPTION OF THE DRAWINGS

Features and advantages of the present invention will become appreciated as the same become better understood with reference to the specification, claims, and appended drawings wherein:

FIGS. 1A and 1B are perspective and top views, respectively, of a prosthetic heart valve and an intercostal incision opening according to an embodiment of the invention;

FIGS. 2A and 2B are perspective views of a prosthetic heart valve support frame in an open/deployed configuration and a folded/delivery configuration, respectively;

FIGS. 3A and 3B are perspective views of a prosthetic heart valve support ring with sewing ring in an open/deployed configuration and a folded/delivery configuration, respectively;

FIGS. 4A-4C are perspective, side (close-up) and perspective views, respectively, of an annuloplasty ring according to an embodiment of the invention;

FIGS. 6A and 6B are perspective and close-up views, respectively, of an upper sewing ring for suture retention on an annuloplasty ring or prosthetic valve in an open/deployed configuration according to an embodiment of the invention;

FIGS. 8A-8C are top, bottom, and side views, respectively, of a handle portion of an annuloplasty ring delivery holder according to an embodiment of the current invention;

FIG. 9 is a schematic depiction of an annuloplasty ring delivery holder according to an embodiment of the invention;

FIGS. 10A and 10B are perspective views of an annuloplasty ring delivery holder with annuloplasty ring in the deployed configuration and stretched/delivery configuration, respectively, according to an embodiment of the current invention;

FIG. 11A is a perspective view of an annuloplasty ring delivery holder with annuloplasty ring in the deployed configuration;

FIG. 11B is a perspective view of the annuloplasty ring delivery holder with annuloplasty ring of FIG. 11A in the stretched/delivery configuration; and FIG. 11C is a perspective view, in close-up, of a portion of the annuloplasty ring delivery holder with annuloplasty ring of FIG. 11A in the deployed configuration.

DETAILED DESCRIPTION OF THE PREFERRED EMBODIMENTS

Figure 5:
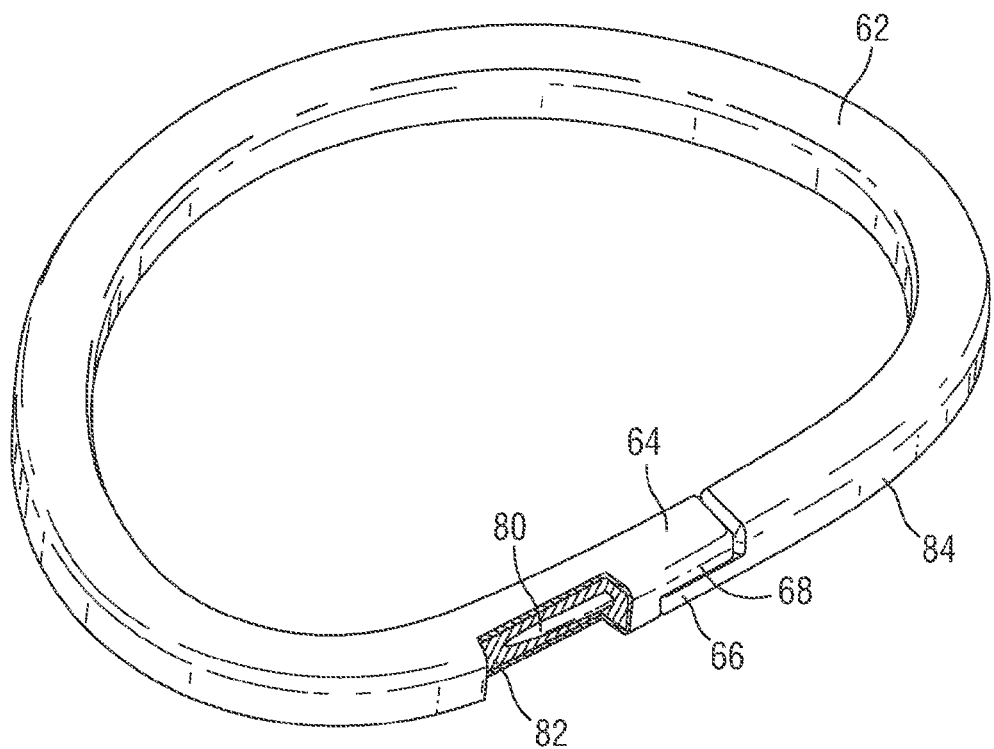
FIG. 5 is a perspective view of an annuloplasty ring main ring body in an open/deployed configuration according to an embodiment of the invention.

An exemplary embodiment of a prosthetic heart valve 10 according to the invention is depicted in FIGS. 1A and 1B. The prosthetic heart valve 10 comprises a support frame 12, commissure posts 14, valve leaflets 16, and sewing ring 18. Hinges (not shown) are provided in the support frame 12 that permit the prosthetic heart valve 10 to fold partially along center hinge lines 22. Valve leaflets 16 extend between commissure posts 14. Note that, for visibility purposes, in FIG. 1A only one of the three valve leaflets is depicted. The valve 10 has an outer diameter 24 and an inner diameter 26, with the inner diameter 26 defining the flow orifice through which blood flows when the leaflets are in the open position. The valve overall height 28 extends from the valve lower surface to the upper tip of the commissure posts 14. Note that the dimensions of a particular valve 10 according to the invention depend on the particular embodiment and desired applications.

An intercostal incision 30 has a length 32 and width 34. The length 32 may be 30 mm or more. The width 34 is typically on the order of about 20 mm. As depicted in FIG. 1B, the heart valve outer diameter 24 of the valve depicted is larger than the intercostal incision width 34, so that the outer diameter 24 is too large for the heart valve 10 to be advanced directly into the intercostal incision 30 without significant manipulation. By folding the heart valve 10 about the hinge lines 22, the valve profile can be reduced to permit the valve 10 to be advanced into the intercostal incision 30.

FIGS. 2A and 2B depict a support frame 12 according to an embodiment of the invention. The support frame 12 has a first half portion 40 and a second half portion 42, with the half portions 40, 42 joined to each other at their respective ends via hinges 44. The hinges 44 permit the half portions 40, 42 to be folded at least partially together, as depicted in FIG. 2B.

In the particular embodiment depicted in FIGS. 2A-2B, the first half portion 40 has a single commissure post position indicated by a commissure hole 46 through which a commissure support (not shown) can be secured (e.g., via suture) when the valve is assembled. The hole 46 and hence the single commissure position of the first half portion 40 is in the center of the first half portion. The second half portion 42 has two commissure post positions, each indicated by a commissure hole 48 through which a commissure support (not shown) can be secured when the valve is assembled. The commissure holes 48 and hence the commissure positions of the second half portion 42 are positioned well away from the center of the second half portion 42. This respective positioning of the commissure holes 46, 48 permits the prosthetic heart valve, when assembled, to be folded without the opposing commissure posts striking each other. Instead, the single commissure post of the first half portion 40 will be advanced to a position in between the two commissure posts of the second half portion 42.

Note that the support frame 12 and its respective elements may be formed of various materials, including metals (such as stainless steel or nitinol) and polymers.

FIGS. 3A and 3B depict the frame 12 with a first sewing ring portion 18a secured to the first half portion 40 and a second sewing rig portion 18b secured to the second half portion 42. The ends 50a of the first sewing ring portion 18a are angled, as are the ends 50b of the second sewing ring portion 18b. The angled surfaces of the respective ends 50a, 50b permit the valve frame 12 to be folded inwardly along the hinges 44, as depicted in FIG. 3B, without the adjacent ends 50a, 50b engaging each other and potentially interfering with the valve folding process.

Note that the heart valve frame and other designs from FIGS. 1A-3B could be applied to an annuloplasty ring according to an embodiment of the invention. Such an annuloplasty ring would have first and second half portions connected via hinges, and could also have angled surface at the adjacent ends of the sewing ring portions for each half portion.

A finished valve (or finished annuloplasty ring) according to an embodiment of the invention, such as that depicted in FIG. 1A, may be biased toward the open configuration (corresponding to the valve configuration depicted in FIG. 1A and the frame configurations depicted in FIGS. 2A and 3A). Such biasing may be achieved via include spring-loading (e.g., in frame, hinges, other structures of the valve) or elastic elements (e.g., in the sewing ring) to the bias frame toward the open position. Memory metals (such as Nitinol) may be used to bias the frame and/or other valve elements to cause the valve, when unrestrained, to return to its open configuration. The finished valve or annuloplasty ring may include a locking mechanism that will hold the valve/ring in the open position. For example, the locking mechanism may be configured to be activated when the valve/ring is released from a holder used to deploy the device. The locking mechanism may be positioned on the frame or other elements of the valve/ring.

An annuloplasty ring 60 according to an embodiment of the invention is depicted in FIGS. 4A-4C. The ring has a main ring body 62 having a first end 64 and a second end 66, with the first end 64 and second end 66 overlapping each other to form a lap joint 68. Secured to the main body 62 is a sewing ring 70, which in the embodiment depicted is secured to the main body 62 at the top thereof using suture ties 72. As depicted in FIG. 4C, the first end 64 can be lifted upward and away (e.g., using mechanical force from some sort of mechanism such as a ring holder portion 74) from the second end 66 to cause the ring 60 to assume a stretched, elongated configuration that may be more easily advanced longitudinally into a port hole and/or intercostal opening. Once the ring is at a desired deployment location (e.g., within a heart valve annulus), the mechanism (e.g., ring holder portion 74) can reposition the first end 64 in overlapping configuration with the second end 66, as depicted in FIGS. 4A and 4B. The annuloplasty ring may include a locking mechanism that can be activated with deployment to prevent the ends 64, 66 from separating after the ring is secured within the patient. For example, a suture line could be passed downwardly through the sewing ring 70 and through the main body 62 at a position 76 at the lap joint 68 so that the suture passes through both the first end 64 and the second end 66, thereby holding the first end 64 against the second end 66 and securing the lap joint 68.

FIG. 5 depicts an embodiment of an annuloplasty ring body 62 having a first end 64 and a second end 66, with the ends 64, 66 overlapping at a lap joint 68. The ring body 62 has an internal structure, such as an internal spring wire 80, which provides structural strength and may also bias the ring toward the open configuration where the ends 64, 66 overlap at the lap joint 68. The internal spring wire may be formed of metals (e.g., stainless steel, nitinol) or polymers or other materials. An internal sewing ring 82 surrounds the internal spring wire 80. The internal sewing ring 82 may be formed from various materials, such as polymers (e.g., thermoplastic), which permit suture to be passed therethrough with relative ease. The internal sewing ring 82 is itself surrounded by a fabric casing 84. Note that the ring body 62 may itself be used as an annuloplasty ring without further elements, e.g., without the need for an additional sewing ring such as the external sewing ring 70 depicted in FIG. 4A.

FIGS. 6A and 6B depict the external sewing ring 70 in greater detail. The external sewing locking ring 70 acts as a suture lock ring, and includes a plurality of sewing holes 90 through which needle and suture may be advanced. The sewing holes 90 can thus serve as guides to indicate positions where suture can most easily and/or effectively be passed into the valve body. Small indentations 92 are provided on the outer and inner perimeters of the external sewing ring, with the small indentations provided to assist in securing the locking ring 70 to the main valve ring body at the time of manufacture. Suture locks 94 are provided to assist in locking the sutures in place. In use, a suture is passed through a first suture lock, then passed through a portion of the native valve annulus, and then passed into another suture lock. In such an embodiment, there is no need to tie knots in the suture to hold the ring in place in the annulus. The external suture ring 70 may be formed from a relatively hard (i.e., needle- and suture-resistant material) that prevents the passage of needle and suture therethrough except through the sewing holes 90.

Note that the annuloplasty ring frame and other designs from FIGS. 4A-6B could be applied to a prosthetic heart valve according to an embodiment of the invention. Such a prosthetic heart valve could have a frame with adjacent ends which could be longitudinally stretched away from each other to form the frame into a somewhat spiral shape, and then allowed to return to their original position to cause the frame to resume the desired configuration for the deployed valve. Note that the frame adjacent ends (e.g., with lap joint) may have to coincide with a commissural post of the heart valve in order to prevent stretching/tearing of any heart valve leaflets that would otherwise cross over the lap joint form the first end to the second end.

Figure 7A:
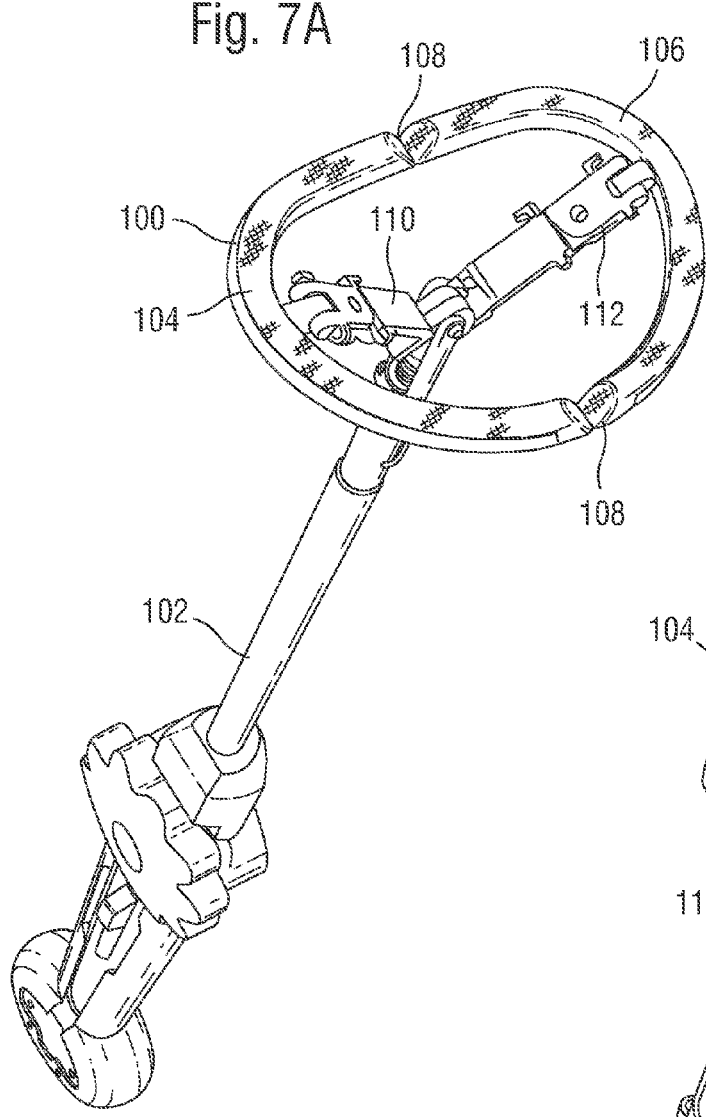
FIGS. 7A and 7B are perspective views of an annuloplasty ring delivery holder with annuloplasty ring in the open/deployed configuration and folded/delivery configuration, respectively, according to an embodiment of the current invention.
Figure 7B:
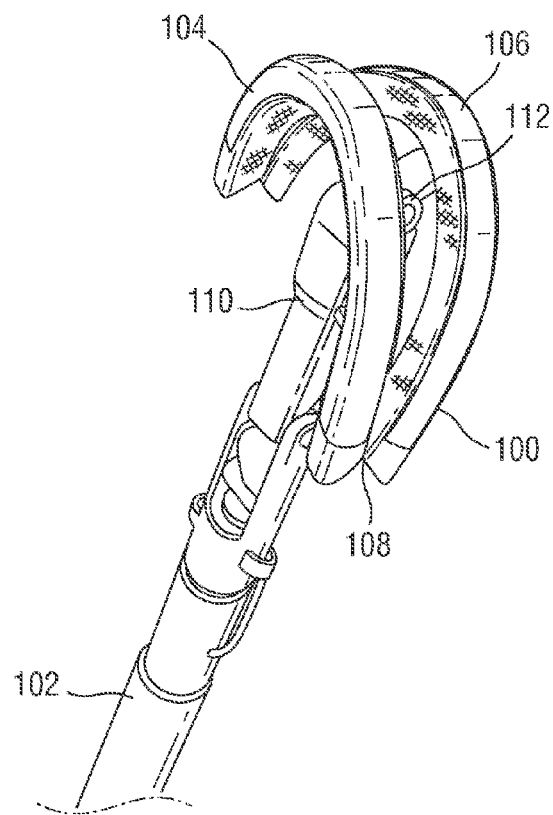

FIGS. 7A and 7B depict an annuloplasty ring 100 secured to device holder 102 according to an embodiment of the invention. The annuloplasty ring 100 is a hinged design similar to the hinged design of the prosthetic heart valve 10 and frame 12 depicted in FIGS. 1A-3B. The annuloplasty ring 100 has a first half 104 and a second half 106, with hinges 108 holding the two halves together. In FIG. 7A, the annuloplasty ring 100 is in its open/deployed configuration, showing the general D-shape of the annuloplasty ring 100. The device holder 102 has a first arm 110 and a second arm 112 releasably secured to the ring first half 104 and second half 106, respectively. In FIG. 7B, the first arm 110 and second arm 112 are drawn together, thereby folding the annuloplasty ring first and second halves 104, 106 together about the hinges 108. The folded annuloplasty ring 100 thus has a lower profile more conducive to advancement into the patient's chest cavity via minimally-invasive methods.

Note that a device holder such as that depicted in FIGS. 7A-7B could be used for delivering and deploying various hinged devices, such as a hinged/foldable prosthetic heart valve such as that depicted in FIGS. 1A-3B.

FIGS. 8A-8C depict the handle portion 120 of the device holder 102, with multiple controls for manipulating the configuration and position of the annuloplasty ring or other prosthetic device being deployed in the patient. The applications of the various controls are depicted schematically in FIG. 9. A device collapse control is provided in the form of an opposing pair of wing levers 122, where inward movement of the wing levers causes the arms 110, 112 to rotate inward against each other and therefore cause a corresponding collapse/hinge-like folding of the device being delivered, and outward movement of the wing levers 122 causes the arms 110, 112 to rotate outwardly away from each other and cause a corresponding unfolding/opening of the device being delivered. A device tipping control is provided in the form of a slider 124 which, when slid forward or backward with respect to the handle 120, causes the device to be tipped in a direction along the z-axis (i.e., out of or into the page) depicted in FIG. 9. A device steering control in the form of a rotatable knob 126 causes, when rotated, left or right turning of the device via left or right turning of the distal end 128 of the holder about a hinge-like connection 130. Note that these controls could be changed in their functions (e.g., the rotatable knob could control the device tipping or device collapse; the slider could control device collapse or device steering; the wing levers could control device tipping or device steering), or entirely different controls or combinations thereof could be used. Other controls are also within the scope of the invention.

Note that the device (e.g., annuloplasty ring or valve) could be secured to the holder via various techniques. The device could be secured to the arms of the holder via sutures, with the sutures being severed once the device is secured in place at the desired implantation site (e.g., the valve annulus). The device could be secured to the holder via clips or other mechanisms, which could be activated from the holder handle to release the device from the holder when desired by the surgeon or other user.

FIGS. 10A and 10B depict an annuloplasty ring 140 secured to a device holder 142 according to an embodiment of the invention. (Note that the device holder 142 could also be used for prosthetic heart valves or other devices.) The annuloplasty ring 140 is of the type depicted in FIGS. 4A-4C, with overlapping first and second ends 144, 146 which can be longitudinally displaced to cause the ring 140 to temporarily assume an elongated spiral form (depicted in FIG. 10B) for advancement through relatively small openings. The holder 142 has first and second arms 148, 150 to which the first and second ends 14a, 146 are secured. The first and second arms 148, 150 which can be longitudinally displaced with respect to each other, thereby causing corresponding longitudinal displacement of the first and second ends 144, 146 with respect to each other to cause the ring to assume an elongated spiral shape. The handle 152 of the holder 142 includes multiple controls, including: a pair of wings 154 to control displacement of the first and second arms 148, 150 (and thus control collapse/elongation of the annuloplasty ring 140 or other device); a slider 156 to control tipping of the distal-most portions of the arms (and therefore of the device secured thereto); and a control knob 158 to control side-to-side movement of the annuloplasty ring 140 or other device.

Another embodiment of a holder 170 for use in deploying an annuloplasty ring 172 or other device capable of stretching into a spiral shape for reduced profile according to the invention is depicted in FIGS. 11A-11C. In FIGS. 11A and 11C, the holder 170 is secured to the ring (e.g., via sutures) with a first overlapping end 174 secured to an upper foot-like element 178 of the holder 170, and a second overlapping end 176 secured to a lower foot-like element 180 of the holder 170. The holder 170 has an upper handle portion 182 and a lower handle portion 184, which can be longitudinally displaced with respect to each other. As depicted in FIG. 11B, when the upper foot-like element 178 is displaced with respect to the lower foot-like element 180 (via movement of the upper handle portion 182 with respect to the lower handle portion 184), the ends 174, 176 of the ring 172 are longitudinally displaced, causing the ring 172 to assume an elongate spiral configuration.

While the invention has been described in its preferred embodiments, it is to be understood that the words which have been used are words of description and not of limitation. Therefore, changes may be made within the appended claims without departing from the true scope of the invention.

What is claimed is:

1. A method of implanting devices in a human body, comprising:
creating an intercostal opening in the chest cavity of a patient;
grasping a device holder having a collapsible and longitudinally elongatable implantable intracardiac device on the distal end thereof, wherein the device is selected from the group consisting of an annuloplasty ring and a prosthetic heart valve;
collapsing the device by operating one or more controls of the device holder to collapse the device;
after collapsing the device, advancing the collapsed device directly through the intercostal opening and into the patient;
positioning the device at an intracardiac deployment site in the patient;
uncollapsing the device so that the device returns to an open and deployed configuration;
securing the device to the deployment site in the patient;
releasing the device from the device holder; and
removing the device holder from the patient, wherein
the implant includes a support ring comprising opposing first and second ends which are positioned adjacent each other when the device is in the open and deployed configuration, the device holder has first and second arms to which the first and second ends are secured, and wherein collapsing the device comprises displacing the first and second arms to space the first and second ends away from each other to thereby cause the support ring to transform to an elongated configuration, and wherein the support ring comprises a support structure which biases the support ring to the open and deployed configuration.

2. The method of claim 1, wherein collapsing the device comprises elongating the device while reducing an outer diameter of the device.

3. The method of claim 1, wherein securing the device to the deployment site comprises securing the device within a native valve annulus.

4. The method of claim 3, wherein securing the device to the deployment site comprises suturing the device within the native valve annulus.

5. The method of claim 1, wherein the elongated configuration of the support ring is an elongated spiral configuration.

6. The method of claim 5, wherein the device holder comprises a proximal portion having a handle with device collapsing and opening controls thereon and a distal portion configured to hold the device and to collapse and open the device responsive to operation of the opening controls of the handle, wherein the device is positioned on the distal portion of the holder.

7. The method of claim 5, wherein the device is configured to collapse to have a minimal profile sufficient to be advanced through an intercostal opening of 20 mm in width.

8. The method of claim 1, wherein the device is an annuloplasty ring and further comprises:
a sewing ring secured around the support ring; and
a cover encapsulating the sewing ring.

9. The method of claim 8, wherein the sewing ring is positioned on an outer perimeter of the device outside a central orifice, the sewing ring configured to receive a needle and suture therethrough.

10. The method of claims 9, further comprising:
a suture locking ring positioned on top of the sewing ring, the suture locking ring comprising:
a plurality of suture holes passing from a top surface of the suture locking ring through to a bottom surface thereof, the suture holes configured to receive suture therethrough; and
a plurality of suture locks on the top surface of the suture locking ring, wherein each suture lock is configured to receive a suture therethrough and to lock the suture in place.

11. The method of claim 1, wherein the device is a prosthetic heart valve comprising:
a plurality of commissural supports extending upward from the device, wherein the commissural supports are spaced around the perimeter of the device, where one of the commissural supports comprises a first half positioned adjacent the first opposing end of the support ring and a second half positioned adjacent the second opposing end of the support ring, wherein when the opposing ends are positioned adjacent each other the first half and second half are positioned against each other and function as a single commissural support, and when the opposing ends are longitudinally displaced from each other the first half and second half are longitudinally displaced from each other.

12. The method of claim 11, further comprising: a plurality of leaflets, wherein each leaflet extends from one commissural support to another commissural support, and wherein when the device is in the open and deployed configuration the leaflets coapt to control fluid flow through a central orifice defined within the support ring, and when the device is in an elongated and spiral configuration the leaflets do not coapt.

13. A method of implanting devices in a human body, comprising:
creating an intercostal opening in the chest cavity of a patient;
grasping a device holder having a collapsible and longitudinally elongatable implantable intracardiac device on the distal end thereof, wherein the device includes a support ring having opposing ends which are positioned adjacent each other when the device is in the an open and deployed configuration, wherein collapsing the device comprises elongating the opposing ends with respect to each other to thereby cause the support ring to transform to an elongated spiral configuration;
collapsing the device by operating one or more controls of the device holder to collapse the device;
after collapsing the device, advancing the collapsed device directly through the intercostal opening and into the patient;
positioning the device at an intracardiac deployment site in the patient;
uncollapsing the device so that the device returns to the open and deployed configuration;
securing the device to the intracardiac deployment site in the patient;

releasing the device from the device holder; and
removing the device holder from the patient.

14. The method of claim 13, wherein the device is selected from the group consisting of annuloplasty rings and prosthetic heart valves, and securing the device to the deployment site comprises securing the device within a native valve annulus.

15. The method of claim 13, wherein securing the device to the deployment site comprises suturing the device within the native valve annulus.

16. The method of claim 13, wherein the support ring comprises a support structure which biases the support ring to the open and deployed configuration.

17. The method of claim 13, wherein the device is an annuloplasty ring and further comprises:
a sewing ring secured around the support ring; and
a cover encapsulating the sewing ring.

18. The method of claim 17, wherein the sewing ring is positioned on an outer perimeter of the device outside a central orifice, the sewing ring configured to receive a needle and suture therethrough.

19. The method of claim 17, further comprising:
a suture locking ring positioned on top of the sewing ring, the suture locking ring comprising:
a plurality of suture holes passing from a top surface of the suture locking ring through to a bottom surface thereof, the suture holes configured to receive suture therethrough; and
a plurality of suture locks on the top surface of the suture locking ring, wherein each suture lock is configured to receive a suture therethrough and to lock the suture in place.

20. The method of claim 13, wherein the device is a prosthetic heart valve comprising:

a plurality of commissural supports extending upward from the device, wherein the commissural supports are spaced around the perimeter of the device, where one of the commissural supports comprises a first half positioned adjacent the first opposing end of the support ring and a second half positioned adjacent the second opposing end of the support ring, wherein when the opposing ends are positioned adjacent each other the first half and second half are positioned against each other and function as a single commissural support, and when the opposing ends are longitudinally displaced from each other the first half and second half are longitudinally displaced from each other.

21. The method of claim 20, further comprising:
a plurality of leaflets, wherein each leaflet extends from one commissural support to another commissural support, and wherein when the device is in the open and deployed configuration the leaflets coapt to control fluid flow through a central orifice defined within the support ring, and when the device is in an elongated and spiral configuration the leaflets do not coapt.

22. The method of claim 13, wherein the device holder comprises a proximal portion having a handle with device collapsing and opening controls thereon and a distal portion configured to hold the device and to collapse and open the device responsive to operation of the opening controls of the handle, wherein the device is positioned on the distal portion of the holder.

23. The method of claim 13, wherein the device is configured to collapse to have a minimal profile sufficient to be advanced through an intercostal opening of 20 mm in width.

* * * * *